United States Patent [19]

Senturia

[11] 4,158,807

[45] Jun. 19, 1979

[54] GAPPED GATE CHARGE-FLOW TRANSISTOR WITH A THIN FILM SENSOR HAVING TWO MODES OF CONDUCTION WITHIN THE GAPPED GATE USED TO SENSE A PROPERTY OF THE AMBIENT ENVIRONMENT

[75] Inventor: Stephen D. Senturia, Cambridge, Mass.

[73] Assignee: Massachusetts Institute of Technology, Cambridge, Mass.

[21] Appl. No.: 790,631

[22] Filed: Apr. 25, 1977

[51] Int. Cl.² .................... G01N 27/00; H01L 29/78; H01L 29/84

[52] U.S. Cl. ................................. 324/71 SN; 357/23; 357/25; 357/26

[58] Field of Search ............... 324/71 SN; 357/23, 25, 357/26

[56] References Cited

FOREIGN PATENT DOCUMENTS 2416883 10/1974 Fed. Rep. of Germany ............. 357/23

OTHER PUBLICATIONS

Catch the Wandering Threshold Voltage, Motorola Monitor; vol. 6, No. 2; Jul. 1968; pp. 18-20.

Wishneusky, John A.; Device Structures for Micro Electronic Gas Sensors; Master's Thesis; MIT; Sep. 1974.

Senturia et al.; The Charge Flow Transistor; Paper Presented at IEEE Meeting; Washington, D. C.; Dec. 7, 1976; Paper 12.8.

Primary Examiner—Robert J. Corcoran
Attorney, Agent, or Firm—Arthur A. Smith, Jr.; Robert Shaw

[57] ABSTRACT

A charge-flow transistor having a gapped gate electrode and a thin-film sensor material in the gap, which sensor material is sensitive to a property of the ambient environment and has a surface conductance that differs substantially from the bulk conductance thereof. The charge-flow transistor is shown as part of an instrument operable to measure said property.

100 Claims, 25 Drawing Figures

ALTERNATIVE CURRENT WAVE

ALTERNATING CURRENT WAVE PLUS NON-ZERO AVERAGE VALUE

GAPPED GATE CHARGE-FLOW TRANSISTOR WITH A THIN FILM SENSOR HAVING TWO MODES OF CONDUCTION WITHIN THE GAPPED GATE USED TO SENSE A PROPERTY OF THE AMBIENT ENVIRONMENT

The Government has rights in this invention pursuant to Grant No. NSG-3061 awarded by the National Aeronautics and Space Administration.

The present invention relates to sensors that operate to sense a property in the surrounding environment and to instruments embodying said sensors.

Attention is called to the Master's thesis of John A. Wishneusky entitled "Device Structures for Microelectronic Gas Sensors," which thesis was deposited in the library system of the Massachusetts Institute of Technology on Oct. 21, 1974 (a copy of the thesis accompanies herewith); a Journal article "The chargeflow transistor: A new MOS device," Senturia et al; Appl. Phys. Lett., Vol. 30, No. 2, 15 Jan. 1977, pp. 106–108; and a paper entitled "The Charge-Flow Transistor," Senturia et al, presented at IEEE, International Electron Device Meeting, Washington, D.C., December 7, 1976, paper 12.8.

Approximately 12,000 people die every year in residential fires in the United States. It has been recognized for several years that widespread installation of early-warning, fire-detection devices can be of significant value in reducing this loss of life and the maiming injuries and property losses due to fires. Federal agencies, such as the National Fire Protection and Control Administration, and many state and local building codes now call for the installation of "smoke detectors" in homes, apartments, hotels, hospitals and nursing homes, and mobile homes. Such detectors must respond to the products of combustion that are given off in the earliest phases of a fire. The detectors must be reliable, sensitive, and relatively free from false alarms. Furthermore, in order to provide a realistic hope of widespread installation in homes, the detectors must be inexpensive. Accordingly, a principal object of the present invention is to provide a low-cost, early-warning, fire-detection device and a low-cost instrument that embodies said device.

There is also widespread need for low-cost devices and instruments to sense other properties such as relative humidity, or the presence of toxic or hazardous gases or vapors. Hence a further object of the present invention is to provide a device to sense a specific property of the environment surrounding the device, the characteristics of the device being tailored to the property being sensed.

There are many methods available for sensing the emanations of fires, humidity, gases or vapors, and other properties. The present invention is based on a particular sensor principle, thin-film conduction. That is, the device exploits the variation of electrical conduction in a suitably chosen thin film of sensor material in response to a variation in the property being sensed. The earliest devices based on the thin-film conduction principle employed an iterdigitated electrode structure on a suitable substrate material coated with the thin-film sensor material. The major disadvantages of these devices are that the devices must be operated at relatively high voltages and at relatively low currents, that elaborate and costly detection circuits are required, and that elaborate electrical shielding of components is required. Accordingly, another object of the present invention is to provide a facile method for exploiting the thin-film conduction principle in practical devices. Specifically, an object is to provide a device, operating on the thin-film conduction principle, that operates at voltage and current levels normally encountered in conventional solid-state circuits, such as MOS circuits (i.e., circuits incorporating Metal-Oxide-Semiconductor Field-Effect Transistors, MOSFETs).

A further object is to provide great simplification of the circuitry required to use the device in an instrument.

A still further object is to provide a device in which the necessity for electrical shielding is obviated.

A still further object is to provide a device that can be fabricated as part of an MOS integrated circuit, combining the sensor device and all associated electronic circuits into a single integrated circuit, thereby achieving maximum reduction of instrument size and cost.

The charge-flow device described in the thesis by John A. Wishneusky does address the aforementioned objects related to the exploitation of the thin-film conduction principal for sensing devices, and provides the basis for the present invention. However, the charge-flow device described by Wishneusky has several practical defects. First, it is based on the bulk resistivity of the thin-film sensor material and on the change in bulk resistivity with the property being sensed. In a gas or vapor sensing device as described by Wishneusky, it would be necessary for the molecules of the gas or vapor to diffuse into the bulk of the film of sensing material before the gas or vapor could be sensed, a process that may take many minutes. Thus, the bulk-resistivity device of Wishneusky has severe response-time limitations. Accordingly, a still further object of the present invention is to provide a charge-flow device with significantly faster response time than the charge-flow device described by Wishneusky.

A second defect in the Wishneusky device is that it has no provision either for biasing of the device at convenient operating points or for monitoring or controlling long-term drifts in device parameters that would affect device sensitivity, device accuracy, and device reliability. Accordingly, still another object of the present invention is to provide a device that can be biased at convenient operating points and a still further object is to provide means for accomplishing that biasing.

A still further object is to provide a method of monitoring long-term drifts in device parameters and compensating for those drifts.

A still further object is to incorporate passivation into the device so as to reduce the occurrence of said long-term drifts.

The device described by Wishneusky operates in only one mode, a mode in which one monitors a time delay. This mode of operation, while convenient for making periodic sampled readings of the property being sensed, is incapable of continuous monitoring of the property being sensed. Hence, a further object of the present invention is to provide a method of using the charge-flow device to provide continuous monitoring or measurement of the property being sensed.

These and still further objects are addressed hereinafter.

The foregoing objects are achieved in a charge-flow transistor that is sensitive to a property of the ambient environment about the transistor. The transistor includes a semiconductor substrate, a source region, a drain region, a gate insulator and a gapped gate electrode comprising a pair of fingers with a gap between the fingers. A thin-film sensor material is disposed within the gap. The sensor material has electrical conductance that is sensitive to a property of the ambient environment within which the transistor is located and the sensor material has a surface conductance that differs substantially from the bulk conductance thereof. Contacts are provided to effect electrical contact to the source region, the drain region and the gate electrode, the contacts being insulated from the substrate and from each other. There is shown an instrument that includes such a charge-flow transistor plus electrical circuitry adapted to sense charge flow in the transistor and relate such charge flow to the environmental property being sensed.

The invention is hereinafter described with reference to the accompanying drawing in which.

Figure 1:
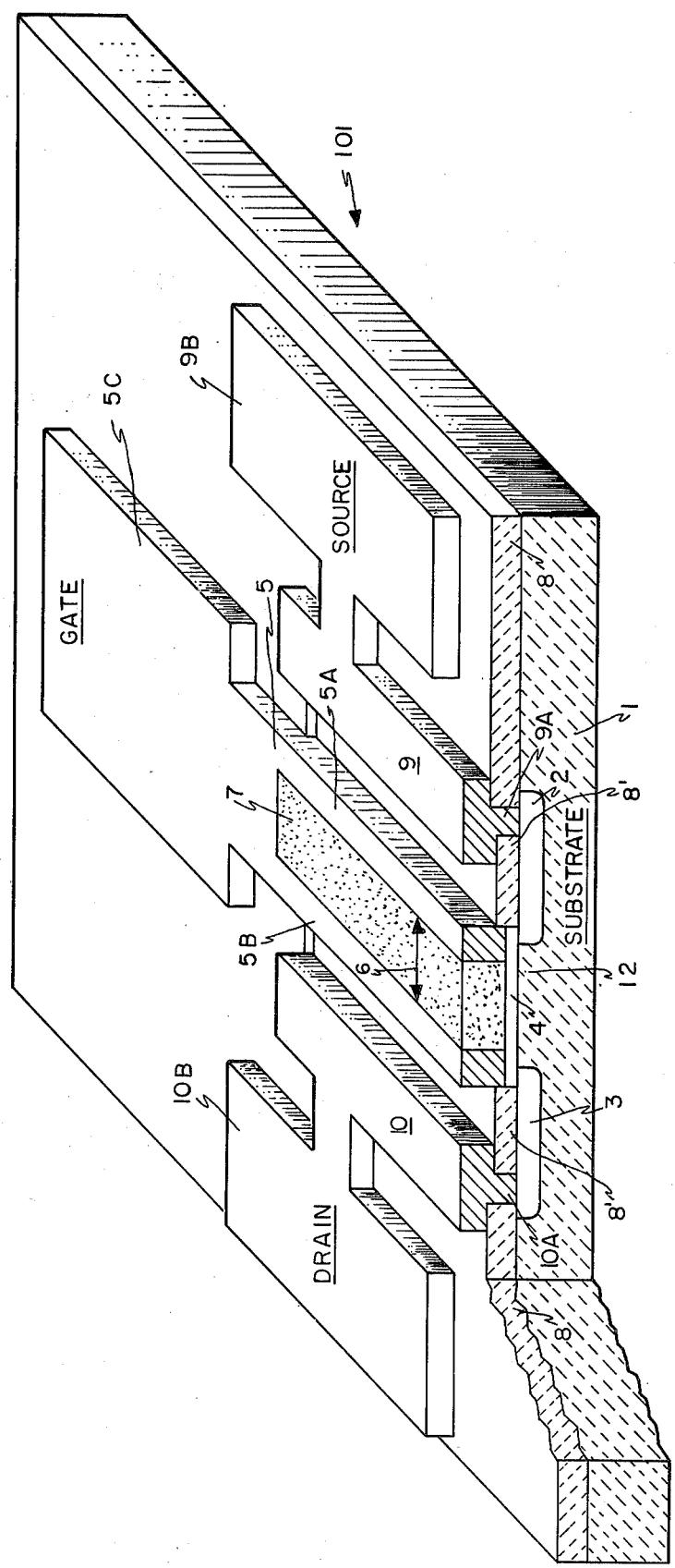
FIG. 1 is an isometric view, on an enlarged scale, partly cutaway and partly diagrammatic in form, showing a charge-flow transistor embodying the present inventive concepts.
Figure 5:
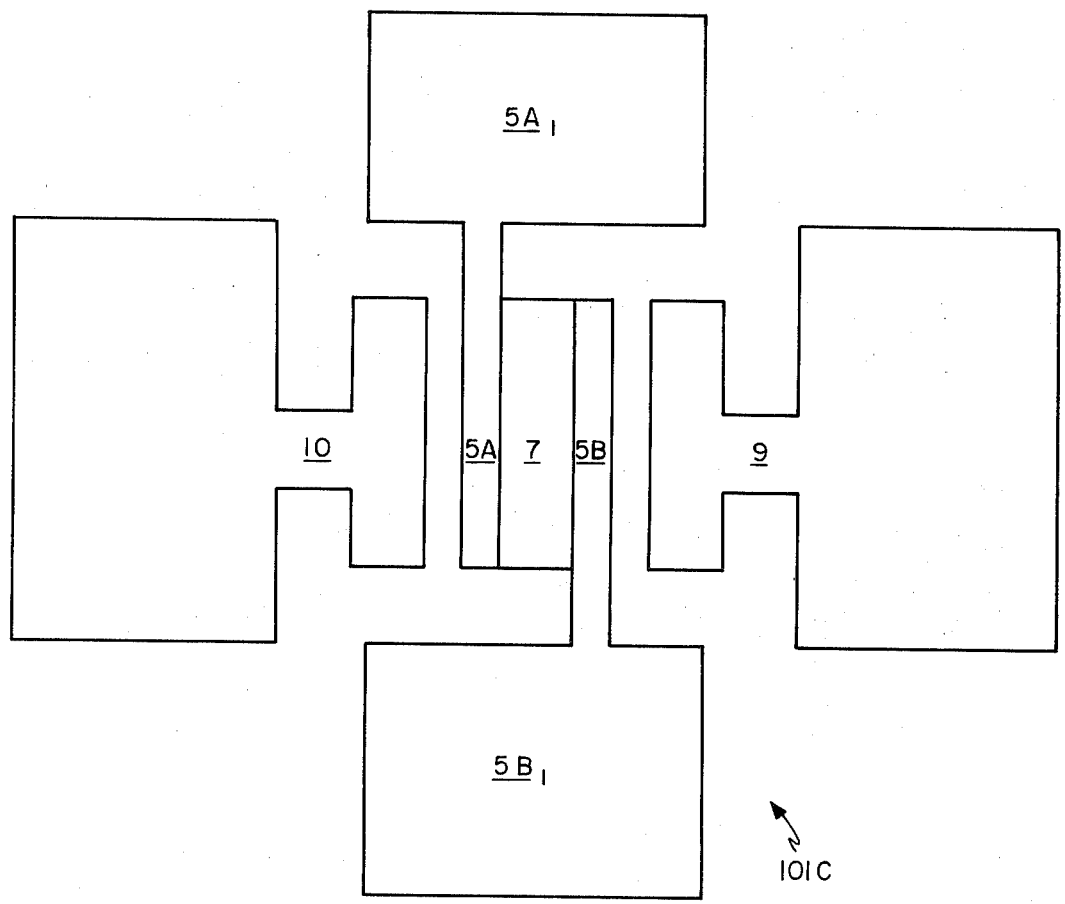
FIG. 5 is a top view of a modification of the transistor of FIG. 1 and shows only those elements of the transistor at the upper surface thereof.
Figure 3A:
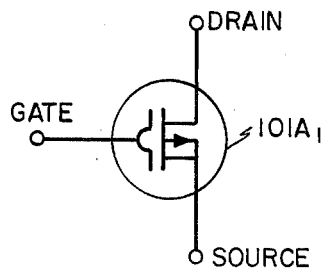
FIGS. 3A, 3B and 3C show, schematically, p-channel charge-flow transistors.
Figure 3B:
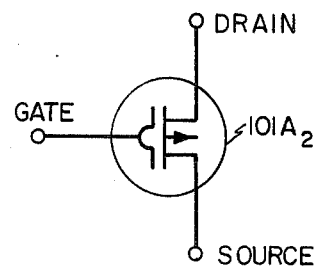
Figure 7:
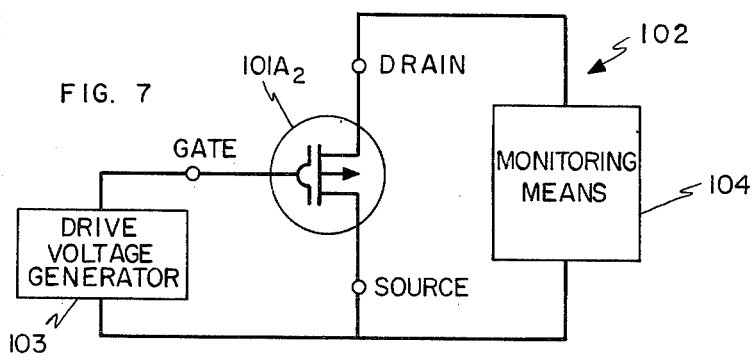
Figure 10:
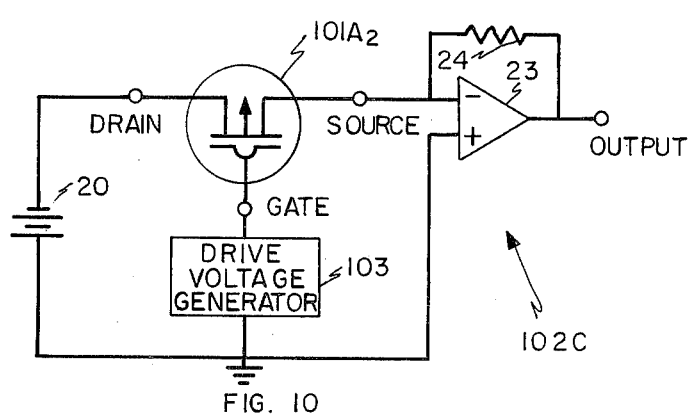
Figure 6:
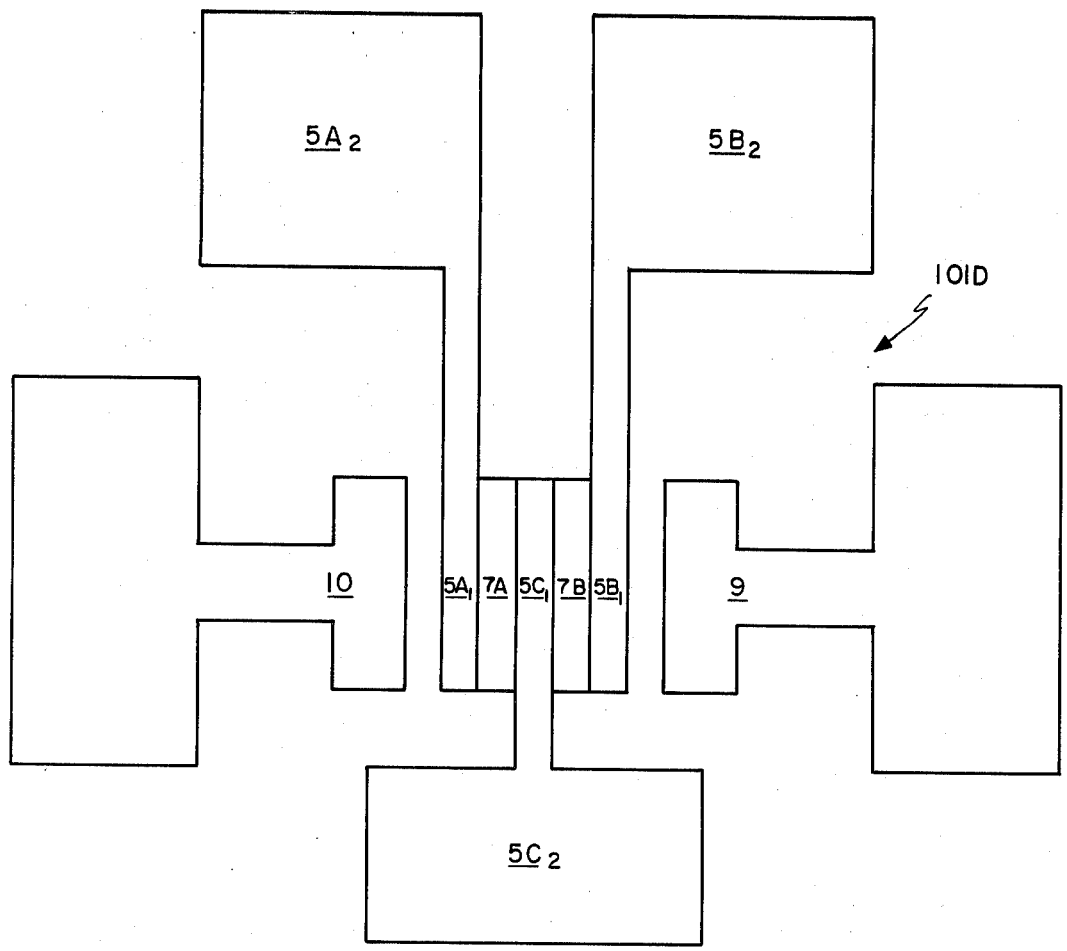
Figure 17:
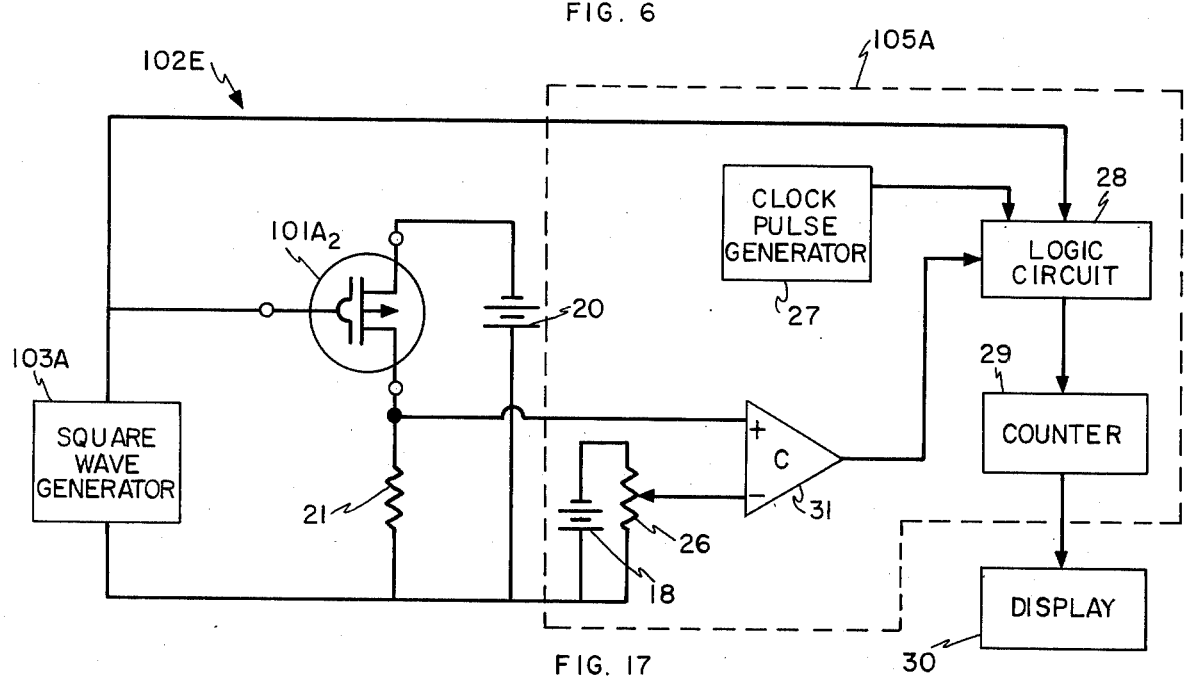
Figure 16:
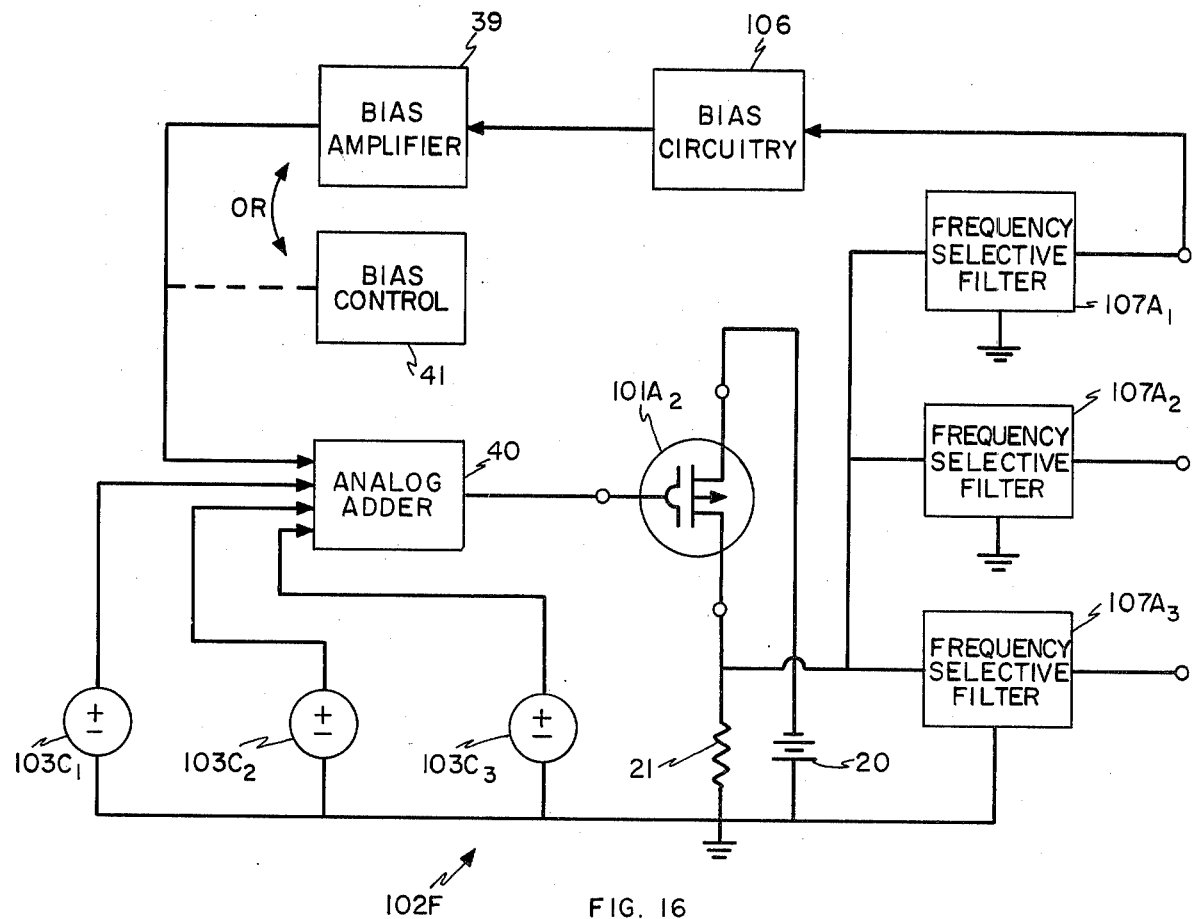
Figure 20:
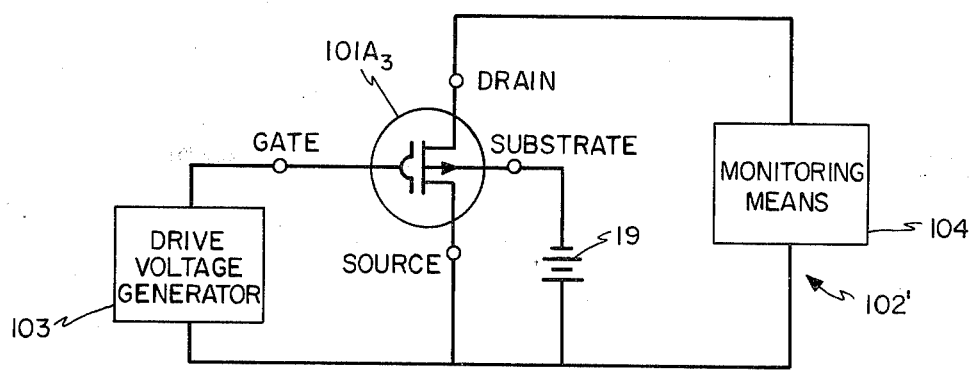
Figure 18:
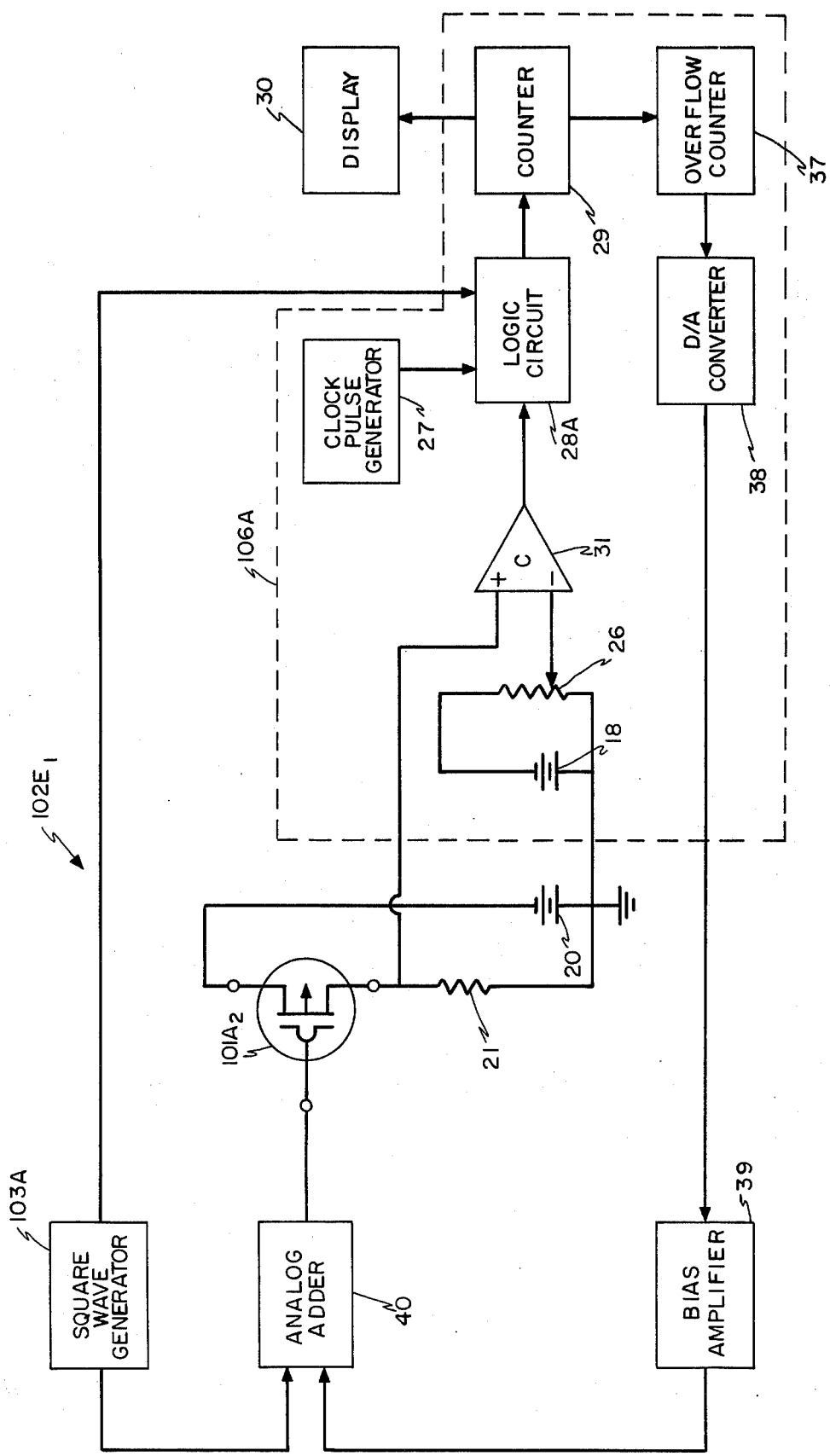
Figure 19:
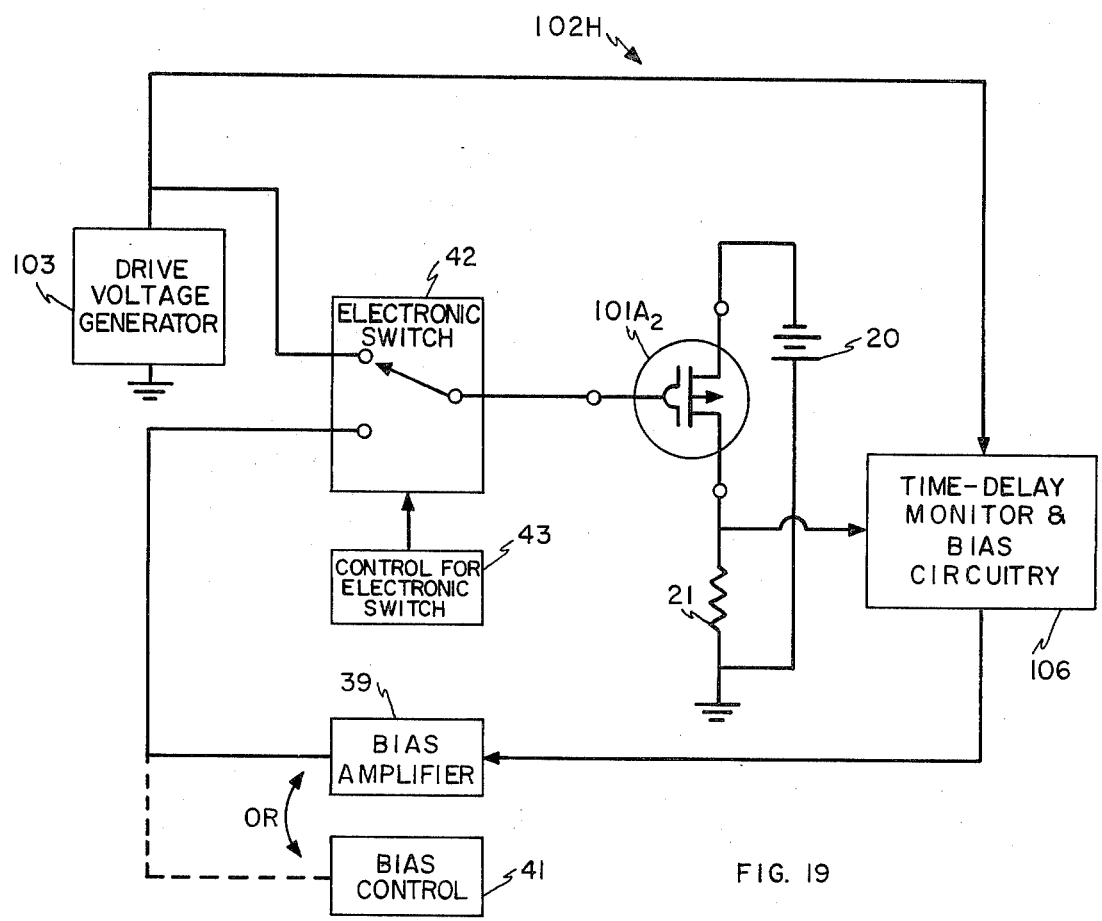
Figure 21:
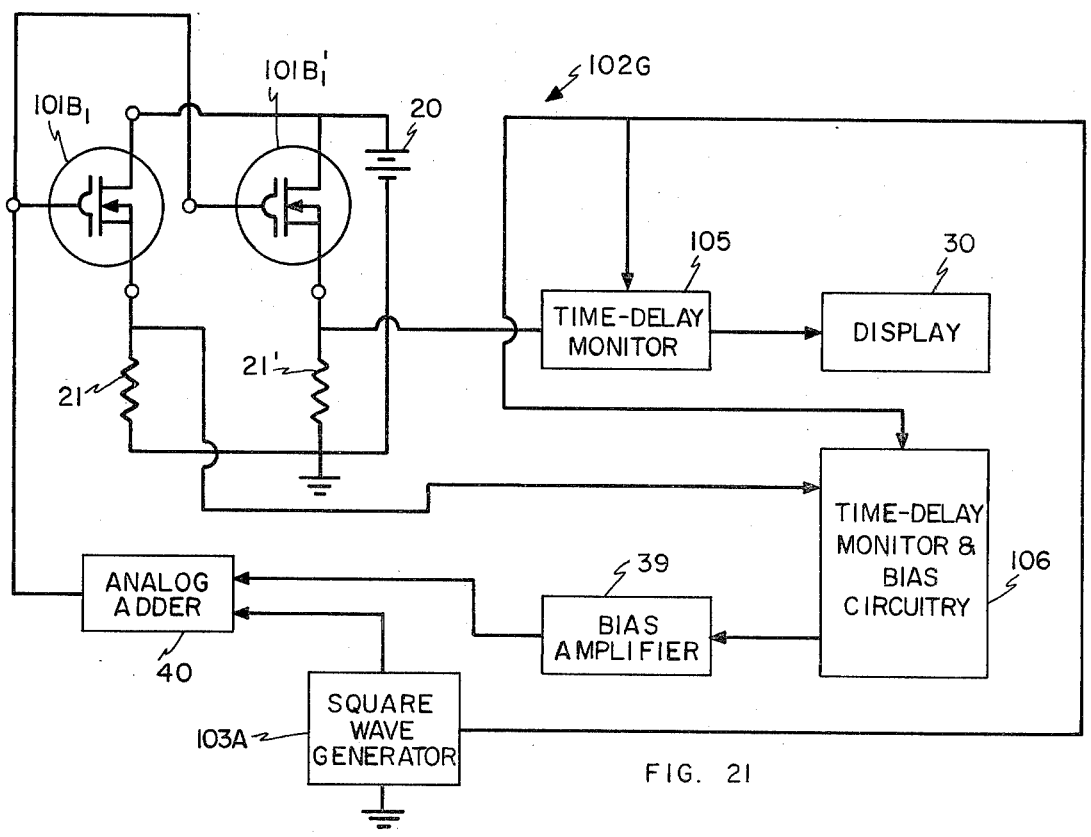

FIG. 6, like FIG. 5, is a top view of a modification of the transistor of FIG. 1 and shows only those elements of the transistor at the upper surface thereof;

FIG. 7 is a block diagram representation of an instrument that includes the transistor of FIG. 3B;

FIGS. 8, 9, 10 and 11 are diagrammatic representations of modifications and/or amplifications of the instrument of FIG. 7;

FIGS. 12, 13, 14 and 15 are diagrams of waveforms that may be generated by the drive-voltage generator of FIGS. 7, 8, 9, 10 and 11;

FIG. 16 is a diagrammatic representation of an instrument that uses waveform generators at several different frequencies and includes provision for feedback bias;

FIG. 17 is a diagrammatic representation of an instrument that is operable to measure the time-delay between the beginning of each cycle of a square wave and the appearance of a complete conducting channel between source region and drain region of a charge-flow transistor;

FIG. 18 is a diagrammatic representation of an adaptation of the instrument of FIG. 17 to include feedback biasing;

FIG. 19 is a diagrammatic representation of an instrument in which an electronic switch is employed to provide alternative application of drive and bias signals;

FIG. 20 is a diagrammatic representation of a modification of the instrument of FIG. 7; and FIG. 21 is a diagrammatic representation of an instrument that includes a plurality of charge-flow transistors.

Turning now to FIG. 1, a charge-flow transistor is shown at 101 comprising a semiconductor substrate 1, a source region 2, a drain region 3, a gate insulator 4, and a gapped gate electrode 5 comprising a pair of fingers 5A and 5B with a gap 6 between the fingers. A thin-film sensor material 7 is disposed within the gap 6; the sensor material 7 has electrical conductance that is sensitive to a property of the ambient environment within which the transistor is located, as discussed in detail hereinafter, and said sensor material has a surface conductance that differs substantially from the bulk conductance thereof.

The device 101 is, of course, a small, flat semiconductor slab or wafer into which has been diffused impurities, as later discussed, to create the source region and the drain region. These regions are often fabricated in identical fashion and are in such a case, electrically equivalent as to function. The upper surface of the slab is covered by thin insulators 8 and 8', except for the portions thereof in electrical contact with a source contact 9A of a source electrode 9, a drain contact 10A of a drain electrode 10, and the gate insulator 4 which is disposed between that portion of the gate electrode 5, comprising the fingers 5A and 5B and the sensor material 7, and the substrate 1. Pads 9B, 5C, and 10B permit electrical contact to the source, gate and drain, respectively, of the device 101, as is well known. The pads are isolated from the substrate by the insulating layer 8 which serves to insulate the contacts or electrodes 5, 9 and 10 from the substrate 1 and from each other. The insulators 8 and 8' can be a thin silicon dioxide layer. Throughout this explanation, the terms "gate," "source," and "drain" are used to designate the electrical connection to the gate region of the device 101, the source region thereof and the drain region thereof, respectively, as is done with respect to more conventional MOS devices.

An important use for the various charge-flow transistors disclosed herein is that of sensing combustion products or some other property in the environment about the transistor. Basic instrumentation to achieve such sensing is shown, for example, at 102 in FIG. 7; the instrument 102 includes a charge-flow transistor $101A_2$, like the transistor 101 in FIG. 1, means 103 for establishing a drive voltage between the gate region and the source region of the transistor $101A_2$, and means 104 for monitoring conduction between the source region and the drain region of the transistor $101A_2$. It is later shown that the symbol used in FIG. 7 designates a p-channel charge-flow transistor with no electrical connection to the substrate. In order to clarify the explanation of the basic operating principle of the charge-flow transistor, the transistor $101A_2$ discussed in this paragraph is further designated to be fabricated such that the transistor $101A_2$ is of the enhancement-mode type. For a p-channel device, this means that there is no conducting channel in that portion of the substrate designated 12 in FIG. 1 between the source region and drain region in the absence of a bias voltage applied by the drive-voltage generator 103 (FIG. 7) between the gate electrode 5 and source region 2 in FIG. 1 (i.e., between the gate and the source in FIG. 7), said channel being caused to appear by the application of a suitable bias between the gate electrode 5 and the source region 2. Other types are discussed later. For the p-channel transistor $101A_2$, said bias voltage must make the potential of the gate electrode 5 negative with respect to the source region 2, and for an enhancement-mode transistor, said bias voltage must exceed in magnitude a certain value, called the threshold voltage, said threshold voltage being the minimum bias voltage at which a conducting channel in the substrate region 12 can be formed. Conduction in the channel 12 is monitored by the monitoring means 104. Because of the structure of the transistor 101, charge must flow in the sensor-material 7, following application of a suitable bias, before a complete channel can be formed in substrate region 12 between the source region 2 and the drain region 3. As a result, depending on the specific waveform produced by the drive-voltage generator 103, the conduction in the channel 12, as detected by monitoring means 104, will exhibit features that depend on the conductivity of the thin-film sensor material. Since said conductivity is sensitive to the property of the ambient being sensed, the conduction in the channel 12 is related to the property being sensed. In the simplest case, in which the drive-voltage generator 103 produces a square wave e.g., the wave labeled 32 in FIG. 12) of sufficient amplitude to exceed th magnitude of threshold voltage and of sufficient period to permit charge-flow process in the thin-film sensor material 7 to reach completion, there is a time delay between the start of a negative half-cycle of the drive waveform (for the p-channel case, as transistor $101A_2$) and the appearance of the conducting channel, said time delay depending on the conductivity of the thin-film sensor material 7.

FIG. 17 shows at 102E an instrument that is a modification of the instrument 102, adapted to measure a time delay. The instrument 102E consists of a transistor $101A_2$, as shown, plus a time delay monitor 105A, comprising a comparator 31, a comparator bias battery 18, a potentiometer 26 to adjust the switch point of the comparator, a clock pulse generator 27, a counter 29, and a logic circuit 28 adapted to clear the counter during the positive half-cycle of the squarewave, to start the counter accumulating clock pulses during the negative-half cycle of the square wave, and to stop the counter when the comparator switches state, indicating that a conduction channel is present in transistor $101A_2$. A display 30 indicates the value of the number in the counter 29, said number being proportional to the time delay.

Figure 3C:
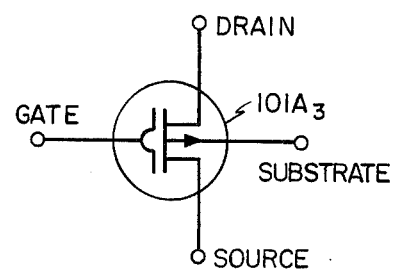
Figure 4A:
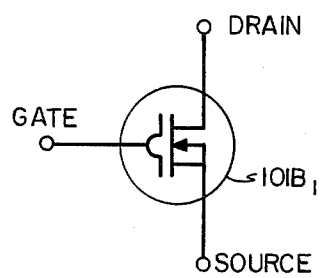
FIGS. 4A, 4B and 4C show, schematically, n-channel charge-flow transistors.
Figure 4B:
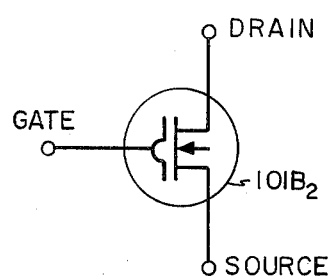
Figure 4C:
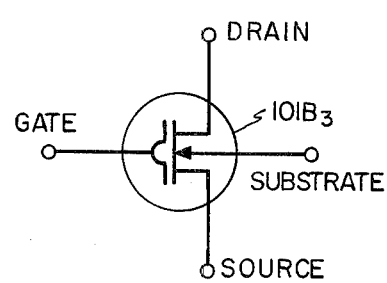

Various types of charge-flow transistors are shown schematically in FIGS. 3A–3C and 4A–4C. FIGS. 3A, 3B, and 3C show p-channel charge-flow transistors $101A_1$, $101A_2$, and $101A_3$, in which the semiconductor substrate is n-type and the source region and drain region are p-type. FIGS. 4A, 4B, and 4C show n-channel charge-flow transistors $101B_1$, $101B_2$, and $101B_3$, in which the semiconductor substrate is p-type annd the source region and drain region are n-type. Both p-channel and n-channel devices are well-known in MOS technology; but, in the case of the charge-flow transistor, there is a new need for both types of devices. Different thin-film sensor materials may have different microscopic electronic properties, some conducting more easily by conduction of electrons, other conducting more easily by conduction of holes. Furthermore, it may be easier to inject one type of carrier or the other into a specific material from the metallic gate electrode. In the charge-flow process described for an enhancement-mode transistor in the preceding paragraph, the polarity of the mobile charge in the thin-film sensor material is opposite to the polarity of the channel. Hence, it is necessary to provide for cases in which the mobile charge in the thin film is positive (the n-channel devices) and in which it is negative (the p-channel devices).

Figure 2:
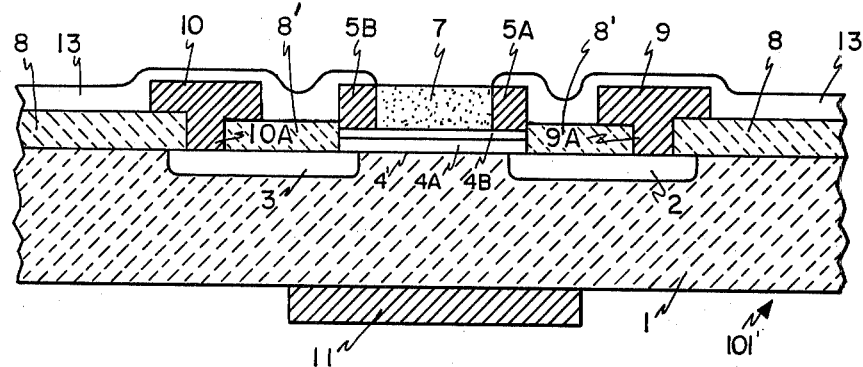
FIG. 2 is a partial section view, on an enlarged scale, of a charge-flow transistor that is a modification of the device of FIG. 1.

The various p-channel devices $101A_1$, $101A_2$ and $101A_3$ differ from one another in the nature of the electrical connection made to the substrate. Corresponding differences are represented for the n-channel devices $101B_1$, $101B_2$, and $101B_3$. FIG. 2 shows a transistor 101', which is a modification of transistor 101, in that the transistor 101' includes, among other things, a contact to the semiconductor substrate 1. The contact 11 can be used to fix the potential of the substrate 1 of the transistor 101' relative to the source 2 thereof. The transistors $101A_1$, and $101B_1$ in FIGS. 3A and 4A, respectively, are schematically represented devices that, like the transistor 101', have a substrate contact 11 and further have this substrate contact connected to the source contact thereof. The transistors $101A_3$ and $101B_3$ in FIGS. 3C and 4C, respectively, are schematically represented devices that, like the transistor 101', have a substrate contact and have a separate external terminal for electrical connection to said substrate contact. Use of the external contact to modify the threshold voltage of a transistor is illustrated in FIG. 20, which shows an instrument 102', similar to instrument 102 of FIG. 7, again comprising a drive voltage generator 103 and monitoring means 104, but having a transistor $101A_3$ and a battery 19 to establish a potential difference between source and substrate. The transistors $101A_2$ and $101B_2$ do not have substrate contacts. All the transistors exhibit the same charge-flow principle of operation of the present invention, but the transistors with substrate connection provide, additionally, flexibility in the use of the transistor.

In addition to the enchancement-mode devices, in which a non-zero bias must be applied between gate and source to create a conducting channel, there is a depletion-mode device in which a conducting channel is present between source and drain in the absence of a bias between gate and source, said channel being made to disappear by the application of a bias between gate and source of suitable polarity and magnitude. In the case of a p-channel depletion-mode transistor, in order to make the channel disappear, the gate potential with respect to the source must be positive and must exceed a certain voltage called a threshold voltage. Depletion-mode charge-flow transistors operate as sensors on the same charge-flow principle as enchancement-mode charge-flow transistors, except that depletion mode devices are "on" in the presence of a bias and enhancement mode devices are "on" in the absence of a bias. Either can be used as a sensor, or both could be used in combination.

With the exception of the techniques for fabricating the gapped gate electrode filled with thin-film sensor material, the fabrication procedures for n-channel and p-channel charge-flow transistors, and for enhancement-mode and depletion mode charge-flow transisitors are based on well-established art, using many of the same techniques widely used in the manufacture of MOSFETs (metal-oxide-semiconductor field-effect transistors) and MOS integrated circuits. In order to simplify this explanation, but without any intent to narrow the broad scope of the present invention, the next paragraph describes in some detail the fabrication of a device like $101A_2$, a p-channel charge-flow transistor without substrate contact, which is used in a system 102 intended to sense the presence of combustion products in the environment about the transistor; later the explanation is expanded to include modification of the transistor for sensing other properties of the environment. The fabrication process as described leads to the fabrication of enhancement-mode p-channel charge-flow transistors.

Fabrication is described with reference to FIG. 1. The substrate 1 is an n-type silicon wafer of 2 inch diameter with a net donor concentration of about $3.5 \times 10^{14}$ cm$^{-3}$. Many identical devices are fabricated on a single wafer. Silicon dioxide is thermally grown over the entire wafer to a thickness of about 5000A. Using standard photomask, photolithography and etching techniques, holes are etched through the oxide above the region designated 2 and 3 in FIG. 1. Boron impurity is deposited using a spin-on borosilica film dopant, and the wafer is heated in a 1200° C. furnace for 30 minutes, resulting in diffused p-type source and drain regions of depth 2.7 μm and surface concentrations of $5 \times 10^{18}$ cm$^{-3}$. After this diffusion process, a thin oxide layer is grown over the source and drain regions. Again, using standard photomask, photolithography, and etching techniques, a hole is etched in this oxide layer at the region designated 4, and a new oxide layer of thickness 1000A is grown by the dry thermal oxidation technique. The results of these steps are a gate insulator 4 of silicon oxide 1000A thick, oxide insulator 8' about 3100A thick, and oxide insulator 8 about 6000A thick. The next step is to use standard photomask, photolithography, and etching techniques to etch holes in the oxide in the locations designated 9A and 10A. A layer of thickness 10,000A of aluminum is then evaporated over the entire wafer to make electrical contacts to source and drain (9A and 10A, repectively), to make the gate electrode 5 and to make the source and drain electrodes (9 and 10 respectively). Using standard photomask, photolithography and etching techniques, the aluminum is then etched away. Specifically, in a departure from standard MOS fabrication technique, this step includes etching away the aluminum in the gap 6 between the fingers 5A and 5B of the gate electrode, leaving the structure of 101 except for the thin film sensor material. The dimensions of importance for a particular device are as follows: the width of the gap 6 is 1 mil, the length of the channel 12 between source and drain is 2 mils, and the length of the finger portion of the gate electrode (i.e., the width of the channel) is 10 mils. The bond pads 9B, 10B and 5C are 6 mil squares. Devices have also been made with gap widths that range from 0.25 mils to 1.5 mils. Many different tecniques, such as deposition from solution, sputtering, or evaporation, can be used for application of the thin film, depending on the specific properties of that material. In the embodiment cited here, the technique used is to deposit a polymer film from a 5% solution in dimethyl formamide using a photoresist spinner to achieve a uniform coating over the entire wafer. Two polymers that are useful for combustion-product sensors are poly (Shiff's base) from p-phenylene diamine and thiophene-2,5-dicarboxaldehyde, and poly (imidazole) from 1,4-bis (phenylglyoxyoyl) benzene and ferrocene-1,1'-dicarboxaldehyde. With either, the thickness of the polymer film is about 3000A. It is not necessary to remove the polymer from the rest of the wafer as it has no influence on device operation except for that portion of the film disposed in the gap 6. The next step is to cut the wafer into individual transistors like 101, or into groups of transistors, using a scribing tool, and mounting individual transistors or groups of transistors onto headers using die-bonding cement. If this cement is electrically conducting, the header serves as substrate contact 11, leading to devices like 101A$_1$ or 101A$_3$. If the cement is an electrical insulator, the device has no substrate connection, like 101A$_2$. The final step is to attach gold wires to the bonding pads using a standard wire bonder. This is done right through that part of the polymer film which covers the bonding pads.

Figure 8:
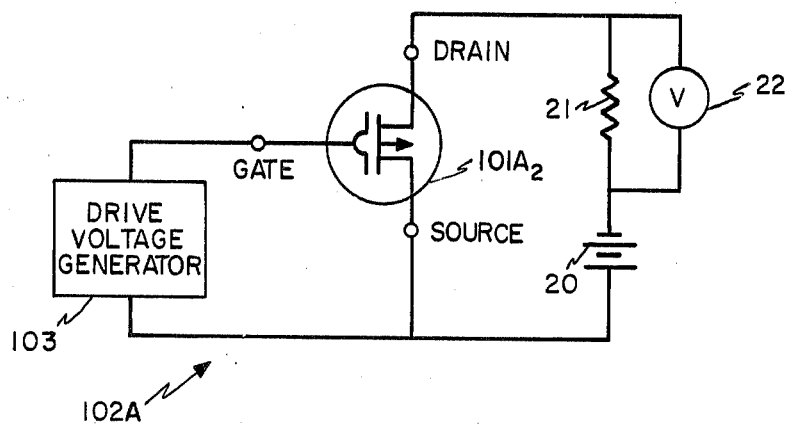
Figure 9:
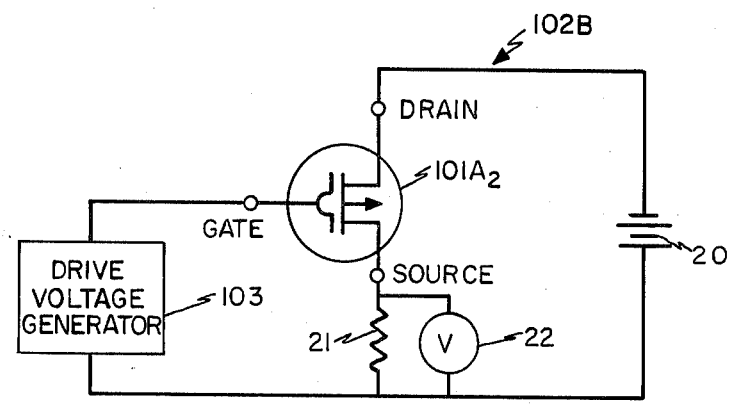

A p-channel enhancement mode transistor 101A$_2$ fabricated according to procedures just described, is then inserted into a circuit such as the circuit designated 102A in FIG. 8. The drive voltage waveform is, for example, the unsymmetrical square wave numbered 33 in FIG. 13 with average value −4 volts and peak-to-peak amplitude 8 volts, the battery 20 is 15 volts, the resistor 21 is 10 kΩ, and the voltmeter 22 is an electrometer. In a specific device coated with the poly (imidazole) and having a threshold voltage of −4 volts, the delay time between the start of the negative half-cycle of the square-wave and the appearance of one microampere of drain current (indicated by a voltage of 10 millivolts on the voltmeter 22) is 17 seconds in the absence of any combustion products, this delay time decreasing to 5 seconds in the presence of combustion products from 10 milligrams of smouldering acrylic fibers in a heater coil. Removal of the smouldering fiber from the vicinity of the transistor causes the delay time to return to a value of 17 seconds, this cycle being reliably repeatable. Similar resuls are obtained with the poly (Schiff's base) polymer and with other smouldering combustibles such as wool, cotton, polyurethane, and polyvinylchloride.

Mention is made above that the surface conductance of the sensor material 7 differs substantially from the bulk conductance thereof; typically the bulk conductance is an order of magnitude smaller than the surface conductance thereof. The need for the effect of such difference in conductance is now explained with reference to the charge-flow transistor 101A$_2$ in FIG. 7 used as a sensor.

The speed of response and the stability of performance are both critical to the utility of a sensing device or instrument. A thin-film material that conducts in two modes, bulk and surface, with the surface conduction being the more rapid of the two, permits not only greatest speed of device response, but it also permits a wide variety of bias schemes to be employed to achieve greater stability of performance.

If the film conducts only in the bulk, then it is necessary, for example, in the case of detection of combustion gases, for the gas molecules to diffuse into the thin film before an appreciable variation of time delay can be observed. If the film conducts more strongly at the surface than in the bulk, two benefits can occur. First, the time delay is shorter, because the charges can move relatively rapidly along the surface of the thin film. Second, provided that the surface conduction is sensitive to the property being sensed, the variation in time delay can appear immediately, without the necessity of waiting for a diffusion process. Thus, the device operates more rapidly, both in terms of the absolute time delay and the speed with which variations in this time delay will occur.

The existence of two modes of conduction also permits new modes of device biasing. If the gate-to-source voltage waveform has a non-zero average value as in FIGS. 13 and 15, then there will be a non-zero average charge at the surface of the thin film. This charge, being attracted by the equal and opposite charge in the substrate, will slowly be conducted through the thin film until it resides at the interface between the thin film and the gate insulator. Once this charge is in the bulk of the film, it is, in effect, stored there, and serves to establish a stable bias point. The amount of stored charge is determined by the average value of the drive voltage, and the speed with which this amount can be charged depends on the bulk conductivity of the film rather than on the more rapid surface conductivity. In a typical device coated with the poly (imidazole) polymer, with response time of a few seconds to combustion products, it takes several days of a drive-voltage with a non-zero average value to shift the stored-charge bias and subsequently several days of a drive voltage with zero average value for the operating point to return to its original value. This stored-charge bias can be used to provide stable long-term operation points that are insensitive to short-term changes in the device ambient.

The instrument 102 of FIG. 7 is shown in more detailed and/or slightly modified form at 102A, 102B, 102C and 102D in FIGS. 8, 9, 10 and 11, respectively, which each contain the transistor $101A_2$ and the waveform generator 103 as the voltage source. The monitoring means 104 in FIG. 7 is shown in FIG. 8 as a power source means comprising the battery 20 and the resistor 21 in series therewith and the voltmeter 22 to note the voltage across the resistor 20, said voltage being proportional to the drain current; in FIG. 9 the battery 20 and the resistor 21 are connected to measure source current which is equal to the drain current; in FIG. 10 the battery 20 is shown connected to the drain and the source current is sensed by an operational amplifier 23 through feedback resistor 24, such that the output of the operational amplifier is proportional to the source current; and in FIG. 11, the source-to-drain current is supplied by a current source 25 whose voltage is monitored by the voltmeter 22 shown. The various circuit configurations are intended to note changes in electric current and/or voltage and to relate the same to the property of the environment being sensed.

Figure 14:
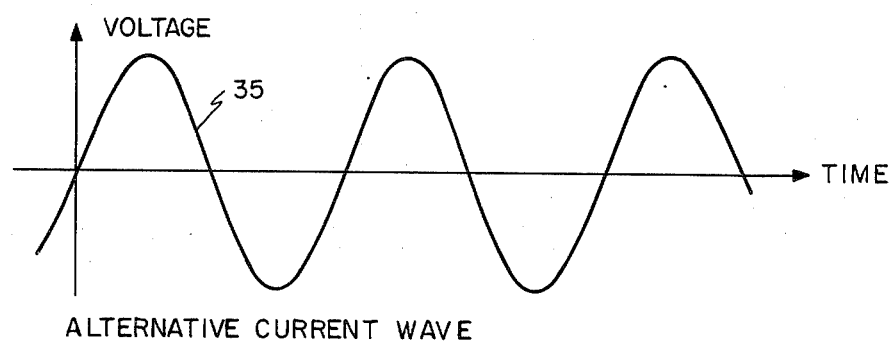
Figure 15:
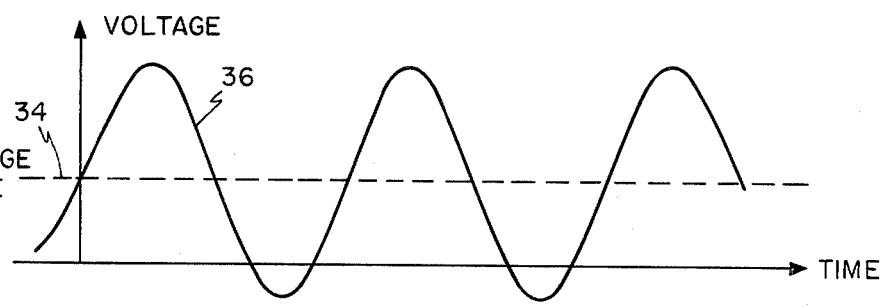
Figure 11:
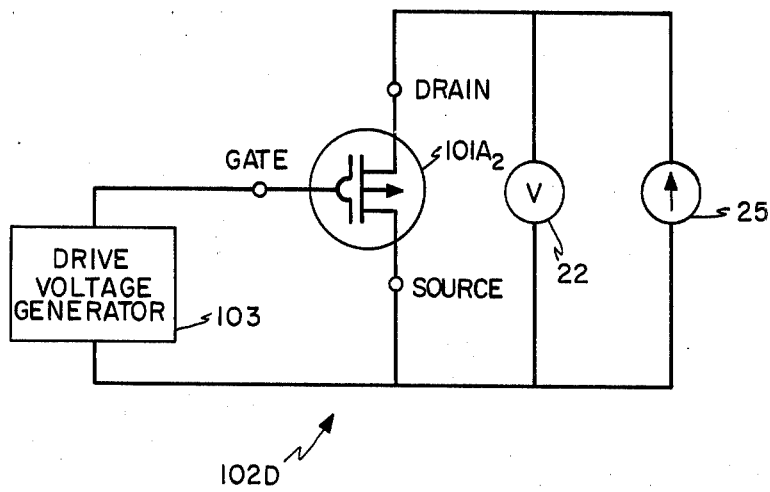
Figure 12:
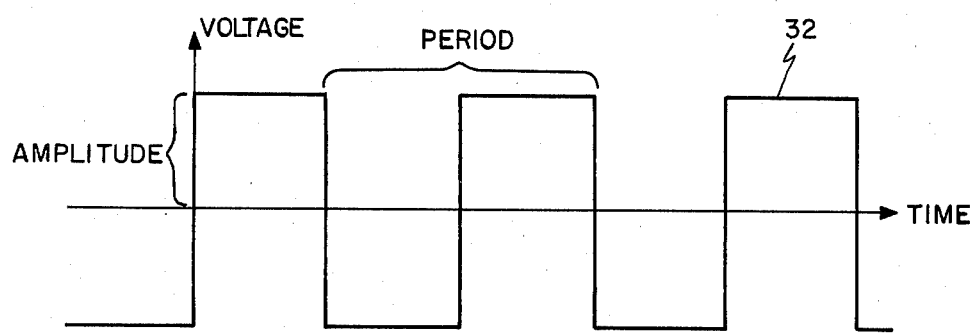
Figure 13:
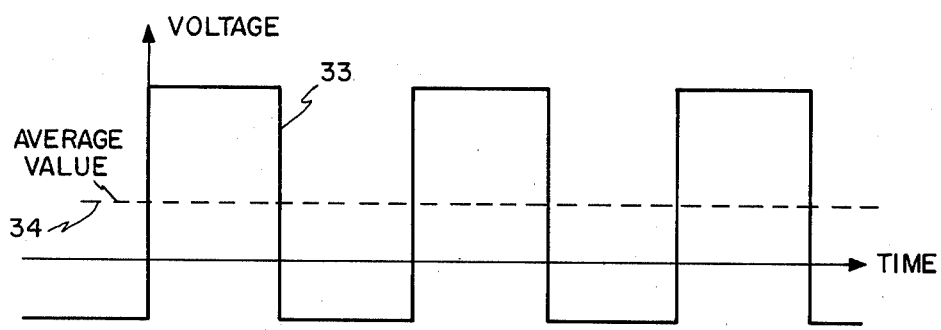

The drive voltage supplied by the waveform generator 103 can be a square wave 32 with zero average value as shown in FIG. 12, a square wave 33 with non-zero average value 34 as shown in FIG. 13, an alternating-current sine wave 35 with zero average value as shown in FIG. 14, an alternating current sine wave 36 with non-zero average value 34 as shown in FIG. 15, or some other current vs time waveform to fit particular sensing functions. The non-zero average value 34 of the source waveform (that is, either the waveform 33 or the waveform 36) serves to establish a bias, as explained in the following paragraph.

The linear mode of operation, referred to hereinafter as class A operation, is explained with reference to the modification 102F of the basic instrument, as shown in FIG. 16. The transistor $101A_2$ in FIG. 16 is, as above discussed, of the p-channel type. Drive-voltage generator 103 is shown comprising an analog adder 40 which adds sinusoidal waveforms at different frequencies from voltage sources $103C_1$, $103C_2$, and $103C_3$ and, also, a bias signal from a bias control 41 or from feedback through suitable bias circuitry 106 and a bias amplifier 39 (an example of the bias circuitry is shown later). In class A operation, the bias signal is adjusted to establish a conducting channel between source and drain. The battery 20, the resistor 21, and three frequency selective filters, $107A_1$, $107A_2$, and $107A_3$, each tuned to one of the sinusoidal sources $103C_1$, $103C_2$, and $103C_3$, form the monitoring means in FIG. 16. Because of the structure of the gapped gate electrode in the transistor $101A_2$, the drain current of the transistor has frequency components at the various frequencies of the drive voltage whose relative amplitudes depend on the conductivity of the thin-film sensor material. Typically, these frequencies are too high to result in a stored-charged bias shift. Hence, only the thin-film surface conductivity affects the frequency components of the drain current. In an embodiment 102F of Class A operation, outputs of the frequence selective filters $107A_2$ and $107A_3$ are used to determine the surface conductivity of the thin film (i.e., to determine the property being sensed by the thin film), and the output of filter $107A_1$ is used to drive the bias circuitry 106 adapted, for example, to feed back that bias voltage that leads to stable output amplitude at the frequency of filter $107A_1$. The bias amplifier 39 accepts the bias signal, and acts as a buffer for the analog adder 40. Alternatively, independent bias control 41 without feedback can be used. The instrument 102F operates as a continuous sensor. Calibration of such an instrument (i.e., an instrument operating as a continuous sensor to provide quantitative data) is accomplished by using standard environments, i.e., known concentrations of the substance being sensed.

A second mode of operation, referred to hereinafter as Class B operation, also makes use of a bias. Here, however, the bias is adjusted very near to the threshold voltage at which the conducting channel appears or disappears. The application of a small additional drive signal, whether square wave of sinusoid, can induce a complete channel and hence a large change in drain-to-source current. The utility of this mode of operation is that very short time delays can be achieved, hence fast response.

A third mode of operation, referred to hereinafter as Class C operation, can be used without a bias or with a bias. The bias point is selected so that a substantial drive signal is required to produce a conducting channel or to make the conducting channel disappear. The most appropriate drive signal for this application is a square wave. The time delay between the application of the square wave and the appearance or disappearance of the conducting channel serves as a measure of the conduction properties of the film. One type of Class C operation uses a square wave with zero average value. A more versatile, but more difficult to control method, uses a square wave with non-zero average value. Because the thin-film bulk conductance permits migration of charge from the surface to the film-oxide interface, it is necessary to provide means to control that bias charge. FIG. 18 shows an instrument $102E_1$, comprising a p-channel charge flow transistor $101A_2$, drive-voltage means comprising a square wave generator 103A, an analog adder 40, and a bias amplifier 39, a battery 20, resistor 21, and monitoring and biasing means 106A comprising a comparator 31, comparator bias battery 18 and comparator bias potentiometer 26, a clock pulse generator 27, a counter 29, an overflow counter 37, a digital-to-analog converter 38, and a logic circuit 28A adapted to clear the counter 29 on the positive half-cycle of the square wave, start the counter accumulating clock pulses on the negative half-cycle of the square wave, stop the counter at the comparator switch point, and periodically reset the overflow counter 27 to zero. A display 30 records the time delay as in FIG. 17. The overflow counter records a count whenever the time delay exceeds the capacity of the counter 20 and, through the D/A converter 38, this serves to shift the bias. Hence, the bias is shifted so that the counter just reaches overflow in the absence of combustion products (or other property being sensed), and a decrease in delay time below this value is indicated in the display 30.

FIG. 19 shows a further adaption 102H in which the stored-charge bias mode is used as the only form of bias.

A bias signal from the time-delay monitor and bias circuitry 106 (of which an example is 106A of FIG. 18) is applied through a bias amplifier 39 to one pole of an electronic switch 42, a drive voltage, such as a square wave, is applied to the other pole from generator 103. Control 43 for the switch 42 produces periodic switching from bias to drive signal, the bias being stored without drift in the transistor 101A$_2$ for a long time (for example, several hours) between rebiasing cycles.

FIG. 21 shows an instrument 102G in which a plurality of transistors 101B$_1$ and 101B$_1$' are used to sense a property; one, the transistor 101B$_1$', is connected to a time-delay monitor 105 and display 30 to indicate the property, another, the transistor 101B$_1$, is connected to a time delay monitor and bias circuit 106 that provides feedback bias for both transistors through a bias amplifier 39 and an analog adder 40.

The charge-flow transistor 101' in FIG. 2, as previously indicated herein, is a modified version of the transistor 101 in FIG. 1. Thus, the gate insulator shown at 4' of the transistor 101' is a two-layer insulator comprising a silicon-dioxide layer 4A and a silicon-nitride (SiN) layer 4B. Also, the device 101' includes means for passivation against contamination that includes a layer 13 (which may be glass) and the silicon-nitride layer 4B. It should be noted at this juncture that some of the sensor materials herein listed may serve also as means for passivation.

The semiconductor substrate may be taken from the group of materials consisting essentially of silicon; germanium; silicon carbide; gallium arsenide or related materials of the class known as III–V compounds; lead telluride and related materials of the class known as IV–VI compounds; and cadmium telluride and related materials of the class known as II–VI compounds.

The bulk conductance of the sensor material 7, as above indicated, is typically much less than the surface conductance, and the surface conductance varies in response to the property of the environment being sensed. Thus, it is the surface conductance changes that are noted and measured as an indication of the presence of the property and the magnitude of the property. The thin-film sensor material of the device being used may be one which is sensitive, say, to the products of combustion of a smouldering fire which is not appreciably sensitive to variations in ambient relative humidity. Such smouldering fire might be, by way of illustration, smouldering wool, smouldering polyvinyl chloride, smouldering polyurethane plastic, or smouldering acrylic fibers. The thin-film sensor material for such sensing functions may be taken from the group consisting essentially of poly (Schiff's base) from p-phenylene diamine and thiophene-2,5-dicarboxaldehyde and poly(imidazole) from 1,4-bis (phenylglyoxyoyl) benzene and ferrocene-1,1'-dicarboxaldehyde. More specifically, a smoke detector built and tested employed the aforementioned poly (imidazole) as the sensing material.

Other properties to be sensed include gas or vapor or oxide combination of gases or vapors; the presence of the products of combustion; the presence of free radicals; the presence of water vapor, the presence of electromagnetic radiation, including microwave, infrared, visible light, ultraviolet light, X-rays, or gamma rays; the presence of subatomic particles; such as beta particles, alpha particles, neutrons; the presence of atomic or molecular beams; changes in ambient pressure, change in ambient temperature; the chemical composition of a solution, the electrochemical potential of a solution.

Other thin-film sensor materials include classes of materials consisting essentially of: organic polymers, metal oxides, oxide glasses, chalcogenide glasses and other amorphous inorganic semiconductors. In this connection, the glasses can perform the dual function of sensing and passivation, as previously discussed.

Portions of modified charge-flow transistor structures are shown in FIGS. 5 and 6. FIG. 5 shows a top view of the top elements only of a charge-flow transistor 101C with two separate contact pads 5A$_1$ and 5B$_1$, respectively for the gate fingers 5A and 5B. Separate contacts permit additional flexibility in setting up charge-flow distribution in the thin-film material 7. Further flexibility is provided by the structure 101D in FIG. 6, showing a top view of the top elements only of a three-finger gate structure comprising fingers 5A$_1$, 5B$_1$, and 5C$_1$, each with separate contact pads 5A$_2$, 5B$_2$, and 5C$_2$, and thin-film materials 7A and 7B disposed in the ga between said fingers, said materials can be the same material, or they can be different the sensor materials. In this case where the materials are different, transistor 101D can combine sensing and logic functions.

Further modifications of the invention herein disclosed will occur to persons skilled in the art and all such modifications are deemed to be within the scope of the invention as defined by the appended claims.

What is claimed is:

1. A charge-flow instrument that comprises, in combination: a charge-flow transistor comprising a semiconductor substrate, a source region, a drain region, a gate insulator, gapped gate electrode means comprising a pair of fingers with a gap between the fingers, a thin-film sensor material disposed in said gap and in electrical contact with said fingers, said sensor material having electrical conductance that is sensitive to a property of the ambient environment within which the transistor is located, said sensor material having a surface conductance that differs substantially from the bulk conductance thereof, that is, the sensor material has two modes of conduction, a surface conductance mode and a bulk conductance mode, contacting means comprising a plurality of contacts for making electrical contact to the source region, the drain region, and the gate electrode means, and insulating means to insulate said contacts from the substrate and from each other; and electric monitoring means connected to the said charge-flow transistor and operable to sense any changes wrought in said surface conductance and to relate the surface conductance and changes therein to said property of the ambient environment.

2. A charge-flow instrument as claimed in claim 1 in which the thickness of the thin film of the transistor is no greater than about one micron.

3. A charge-flow instrument as in claim 1 in which the contacting means is also provided with means for making electrical contact to the substrate of the transistor.

4. A charge-flow instrument as claimed in claim 1 wherein the thickness of the gate electrode of the transistor is comparable to that of the thin-film sensor material.

5. A charge-flow instrument in claim 1 in which the source region of the transistor and the drain region are fabricated identically and are, thus, electrically interchangeable.

6. A charge-flow instrument as in claim 1 which includes means for passivation of the transistor against contamination.

7. A charge-flow instrument as in claim 6 in which the sensor material also serves as means for passivation.

8. A charge-flow instrument as in claim 6 in which the means for passivation comprises separate passivation means for the gate insulator and for the transistor as a whole.

9. A charge-flow instrument as in claim 8 in which the sensor material also serves as part of the means for passivation.

10. A charge-flow instrument as in claim 1 in which the semiconductor substrate of the transistor is n-type and the source region and the drain region are p-type, this configuration being called a p-channel charge-flow transistor.

11. A charge-flow instrument as in claim 10 in which a conducting channel is present between the source region and the drain region of the charge-flow transistor in the absence of a bias voltage between the gate electrode means and the source region, said conducting channel being caused to disappear by the application of a suitable bias voltage between the gate electrode and the source region.

12. A charge-flow instrument as in claim 10 in which there is no conducting channel between the source region and the drain region of the charge-flow transistor in the absence of a bias voltage between the gate electrode means and the source region, said conducting channel being established by the application of a suitable bias voltage between the gate electrode and the source region.

13. A charge-flow instrument as in claim 1 in which the semiconductor substrate of the transistor is p-type and the source region and the drain region are n-type, this configuration being called an n-channel charge-flow transistor.

14. A charge-flow instrument as in claim 13 in which a conducting channel is present between the source region and the drain region of the transistor in the absence of a bias voltage between the gate electrode means and the source region, said conducting channel being caused to disappear by the application of a suitable bias voltage between the gate electrode and the source region.

15. A charge-flow instrument as in claim 13 in which there is no conducting channel between the source region and the drain region of the transistor in the absence of a bias voltage between the gate electrode means and the source region, said conducting channel being established by the application of a suitable bias voltage between the gate electrode and the source region.

16. A charge-flow instrument as in claim 1 in which the semiconductor is taken from the group of materials consisting essentially of silicon; germanium; silicon carbide; gallium arsenide or related materials of the class known as III-V compounds; lead telluride and related materials of the class known as IV-VI compounds; cadmium telluride and related materials of the class known as II-VI compounds.

17. A charge-flow instrument as in claim 1 in which the gate insulator of the transistor comprises silicon dioxide.

18. A charge-flow instrument as in claim 17 wherein the silicon dioxide is combined with silicon nitride.

19. A charge-flow instrument as in claim 17 in which the gate insulator is silicon dioxide of thickness between 50 angstroms and 10,000 angstroms.

20. A charge-flow instrument as in claim 1 in which the property being sensed is one of the following: the presence of a gas or vapor or a combination of gases or vapors; the presence of the products of combustion; the presence of free radicals; the presence of water vapor; the presence of electromagnetic radiation, including microwave, infrared, visible light, ultraviolet light, X-rays, or gamma rays; the presence of subatomic particles, such as beta particles, alpha particles, neutrons; the presence of atomic or molecular beams; changes in ambient pressure; changes in ambient temperature; the chemical composition f a solution; the electrochemical potential of a solution.

21. A charge-flow instrument as in claim 1 in which the thin-film sensor material of the transistor is taken from the classes of materials consisting essentially of: organic polymers; metal oxides; oxde glasses; chalcogenide glasses and other amorphous inorganic semiconductors.

22. A charge-flow instrument as in claim 1 in which the bulk sheet conductance of the sensor material of the transistor is at least an order of magnitude smaller than the surface conductance thereof.

23. A charge-flow instrument as in claim 22 in which the surface conductance of the thin-film sensor material varies in response to the property being sensed.

24. A charge-flow instrument as in claim 1 in which the thin-film sensor material of the transistor is sensitive to the products of combustion of a smouldering fire, but which is not appreciably sensitive to variations in ambient relative humidity.

25. A charge-flow instrument as in claim 24 in which the fires to which the device is sensitive include smouldering cotton, smouldering wool, smouldering polyvinyl chloride, smouldering polyurethane plastic, or smouldering acrylic fibers.

26. A charge-flow instrument as in claim 24 in which the thin-film sensor material is taken from the group consisting essentially of poly (Schiff's base) from p-phenylene diamine and thiophene-2,5-dicarboxaldehyde and poly (imidazole) from 1,4-bis (phenylglyoxyoyl) benzene and ferrocene-1,1'-dicarboxaldehyde.

27. A charge-flow instrument as in claim 26 in which the semiconductor substrate is silicon.

28. A charge-flow instrument as in claim 27 which is of the enhancement-mode p-channel type.

29. A charge-flow instrument as in claim 28 in which the threshold bias voltage at which a conducting channel appears between source region and drain region has magnitude in the range 1-25 volts.

30. A charge-flow instrument as in claim 28 in which the gate insulator comprises a 1000-angstrom layer of silicon dioxide.

31. A charge-flow instrument as in claim 30 in which the gap in the gate electrode is in the rane 0.25 to 1.5 mils.

32. A charge-flow instrument as in claim 31 in which the gate electrode means and the contacting means to the source region and the drain region comprise aluminum.

33. A charge-flow instrument as in claim 1 in which the gap in the gate region is between 0.05 mils and 5.0 mils in width.

34. A charge-flow instrument as in claim 1 in which the thin-film sensor material is applied either from solution, by evaporation, by sputtering, or by direct chemical deposition.

35. A charge-flow instrument as in claim 1 in which the gate electrode means comprises a plurality of fingers, each with separate electrical contacts, to provide means for independent biasing of each finger of the gate electrode.

36. A charge-flow instrument as in claim 1 wherein the electric monitoring means includes means for establishing a drive voltage between the gate region and the source region of the transistor.

37. An instrument as in claim 1 in which said electric monitoring means comprises in combination: power source means connected to establish a voltage difference between the source region and drain region; and means for sensing current flow between the source region and the drain region.

38. An instrument as in claim 1 in which said electric monitoring means comprises, in combination: power source means connected to establish a current between the source region and drain region; and means for sensing the voltage differences between the source region and the drain region.

39. A charge-flow instrument as in claim 36 in which the drive voltage is a square wave.

40. A charge-flow instrument as in claim 39 in which the time delay between a transition in the square wave and the appearance or disappearance of a complete conducting channel between the source region and the drain region is used as a measure of the property being sensed by the instrument.

41. A charge-flow instrument as in claim 40 in which the amplitude and period of the square-wave are adjusted to provide time delays in the range $10^{-3}$ seconds to 100 seconds.

42. A charge-flow instrument as in claim 36 in which the drive voltage is an alternating-current wave.

43. A charge-flow instrument as in claim 42 wherein the alternating-current wave is a sine wave.

44. A charge-flow instrument as in claim 36 in which the means for establishing a drive voltage between the gate region and the source region is operable to establish a drive voltage with a non zero average value, said average value establishing a bias voltage between the gate region and the source region.

45. A charge-flow instrument as in claim 44 in which the drive voltage is a square wave with a non-zero average value.

46. A charge-flow instrument as in claim 44 in which the drive voltage can be represented as a non-zero average value plus an alternating-current waveform.

47. A charge-flow instrument as in claim 46 wherein the alternating current wave is a sine wave.

48. A charge-flow instrument as in claim 44 in which the bias voltage is adjusted such that there is a conducting channel between the source region and the drain region at all times, this being called Class A operation.

49. A charge-flow instrument as in claim 48 in which the drive voltage includes a plurality of sine waves at different frequencies.

50. A charge-flow instrument as in claim 49 in which means is provided for measuring separately the frequency components of the voltage and/or current between the source region and the drain region.

51. A charge-flow instrument as in claim 50 in which at least one of the frequency components of said voltage and/or current is used to provide a measure of the property of the environment being sensed by the instrument.

52. A charge-flow instrument as in claim 51 in which at least one of said frequency components is used to provide feedback means for adjusting the bias.

53. A charge-flow instrument as in claim 44 in which the bias voltage is adjusted near that threshold voltage at which the conducting channel between the source region and the drain region either appears or disappears, this being called Class B operation.

54. A charge-flow instrument as in claim 53 in which the drive voltage consists of a square wave with non-zero average value.

55. A charge-flow instrument as in claim 54 in which the time delay between a transition in the square wave and the appearance or disappearance of a complete conducting channel between the source region and the drain region is used as a measure of the property being sensed by the instrument.

56. A charge-flow instrument as in claim 55 in which said time delay is also used to provide feedback means to adjust the bias.

57. A charge-flow instrument as in claim 44 in which the bias voltage is adjusted such that there would be no conducting channel between the source region and drain region without the additional effect of a large time-varying part of the drive voltage, this being called or termed Class C operation.

58. A charge-flow instrument as in claim 57 in which the drive voltage consists of a square wave with non zero average value.

59. A charge-flow instrument as in claim 58 in which the time delay between a transition in the square wave and the appearance or disappearance of a complete conducting channel between the source region and the drain region is used as a measure of the property being sensed by the instrument.

60. A charge-flow instrument as in claim 59 in which said time delay is also used to provide feedback means to adjust the bias.

61. A charge-flow instrument as in claim 44 that includes feedback means to adjust the bias voltage to compensate for long-term drifts in the transistor threshold voltage.

62. A charge-flow instrument as in claim 36 in which means is also provided for alternate switching of the drive voltage between two electric sources, one operable to establish a time-varying drive signal.

63. A charge-flow instrument as in claim 62 in which said time-varying drive signal is a square wave with zero average value.

64. A charge-flow instrument as in claim 62 in which said time-varying drive signal is a sine wave with zero average value.

65. An instrument as in claim 44 that includes a plurality of charge-flow transistors, said electric monitoring means being connected to apply a drive voltage to each of the transistors such that, at any instant of time, at least one of the charge-flow transistors is being used as a sensor and at least one of said plurality is being used to determine bias parameters.

66. A charge-flow instrument as in claim 36 that senses the presence of products of combustion in said environment.

67. A charge-flow instrument as in claim 66 that senses the presence of products of combustion but is not appreciably sensitive to variations in humidity.

68. A charge-flow instrument as in claim 67 in which the thin-film sensor material is sensitive to the products of combustion of a smouldering fire, but which is not appreciably sensitive to variations in ambient relative humidity.

69. A charge-flow instrument as claimed in claim 68 wherein said fires to which the sensor material is sensitive include smouldering cotton, smouldering wool, smouldering polyvinyl chloride, smouldering polyurethane plastic, or smouldering acrylic fibers.

70. A charge-flow instrument as claimed in claim 68 wherein the thin-film sensor material is taken from the group of materials consisting essentially of a poly (Schiff's base) from p-phenylene diamine and thiopene-2,5-dicarboxaldehyde or poly (imidazole) from 1,4-bis (phenylglyoxyoyl) benzene and ferrocene-1,1'-dicarboxaldehyde.

71. A charge-flow instrument as in claim 70 in which the semiconductor substrate is silicon.

72. A charge-flow instrument as in claim 71 which is of the enhancement-mode p-channel type.

73. A charge-flow instrument as in claim 72 in which the threshold bias voltage at which a conducting channel appears between source region and drain region has magnitude in the range 1–25 volts.

74. A charge-flow instrument as in claim 72 in which the gap in the gate region is between 0.05 mils and 5.0 mils in width.

75. A charge-flow instrument as in claim 72 in which the gate insulator comprises a 1000-angstrom layer of silicon dioxide.

76. A charge-flow instrument as in claim 75 in which the gap in the gate electrode means is in the range 0.25 to 1.5 mils.

77. A charge-flow instrument as in claim 76 in which the gate electrode means comprises aluminum of thickness in the range 50–20,000 angstroms.

78. A charge-flow instrument as in claim 77 in which the sensor material is applied by spinning from a 5% solution in dimethyl formamide.

79. An instrument as in claim 36 in which said charge-flow transistor also has contacting means to make electrical contact to the substrate.

80. An instrument as in claim 79 which includes substrate bias means for establishing a substrate bias voltage between the substrate and the source region.

81. An instrument as in claim 80 in which said substrate bias is operable to modify the threshold voltage at which the conducting channel between the source region and the drain region either appears or disappears.

82. A charge-flow instrument as in claim 36 that includes a plurality of charge-flow transistors and means for combining the sensed outputs of said transistors.

83. An instrument as in claim 82 in which the combined outputs of said transistors are used as a measure of the property being sensed.

84. A charge-flow instrument as in claim 65 in which feedback means is provided to adjust the bias to compensate for drifts in threshold voltage.

85. An instrument that comprises, in combination: a charge-flow transistor comprising a semiconductor substrate, a source region, a drain region, a gate insulator, a gapped gate electrode, a thin-film sensor material disposed in the gap of the gate electrode, said sensor material having electrical conductance that is sensitive to a property of the ambient environment within which the transistor is located, said sensor material having a surface conductance that differs substantially from the bulk conductance thereof, that is, the sensor material has two modes of conductance, a surface conductance mode and a bulk conductance mode, and contacting means for making electrical contact to the source region, the drain region, and the gate electrode; and electric monitoring means connected to said charge flow transistor and operable to sense any changes wrought in said surface conductance and to relate the surface conductance and changes therein to said property of the ambient environment.

86. A charge-flow transistor as claimed in claim 85 in which the thickness of the thin film is no greater than about one micron.

87. A charge-flow instrument as in claim 85 in which the contacting means of the transistor is also provided within means for making electrical contact to the substrate.

88. A charge-flow instrument as in claim 85 which includes means for passivation of the transistor against contamination.

89. A charge-flow instrument as in claim 88 in which the sensor material also serves as means for passivation.

90. An instrument that comprises: a charge-flow transistor comprising a semiconductor substrate, a source region, a drain region, a gate insulator, gapped gate electrode means and a thin-film sensor material disposed in the gap of said gapped gate electrode means and in electrical contact therewith, said sensor material having electrical conductance that is sensitive to a property of the ambient environment within which the transistor is located, said sensor material having two modes of conduction, a surface conductance mode and a bulk conductance mode, wherein the surface conductance thereof differs substantially from the bulk conductance thereof; and electric monitoring means connected to said charge-flow transistor and operable to sense any changes wrought in said surface conductance and to relate the surface conductance and changes therein to said property of the ambient environment.

91. An instrument as claimed in claim 90 wherein said bulk conductance is at least about an order of magnitude smaller than the surface conductance thereof.

92. A charge-flow instrument as claimed in claim 1 in which the gate insulator of the transistor comprises silicon dioxide in combination with another material.

93. A charge-flow instrument as claimed in claim 1 in which said contacting means comprises a contact pad electrically shorting the ends of the pair of fingers.

94. An instrument as claimed in claim 90 in which the bulk conductance of the thin-film sensor material is much smaller than the surface conductance thereof.

95. An instrument as claimed in claim 90 wherein the thin-film sensor material of the transistor is poly (imidazole) from 1,4-bis (phenylglyoxyloyl) benzene and ferrocene-1,1'-dicarboxaldehyde.

96. An instrument as claimed in claim 90 wherein the thin-film sensor material of the transistor is a weakly conducting semiconductor.

97. An instrument as claimed in claim 44 that includes digital means and D/A means that act, in combination, to adjust the bias voltage and, hence, maintain said bias at about the threshold voltage of the transistor in the absence of said property of the ambient environment.

98. An instrument as claimed in claim 90 in which the bulk conductance of the thin film sensor material is about an order of magnitude smaller than the surface conductance thereof.

99. Apparatus that comprises, in combination: a charge-flow transistor comprising a semiconductor substrate, a source region, a drain region, a gate insulator, gapped gate electrode means, a thin-film sensor material disposed in the gap of the gate electrode and in electrical contact therewith, said sensor material having electrical conductance that is sensitive to a property of the ambient environment within which the transistor is located, said sensor material having two modes of conduction that differ substantially from one another; and electric monitoring means connected to said charge-flow transistor and operable to sense one mode of conductance and any changes wrought in said one mode of conductance and to relate said one mode of conductance and changes therein to said property of the ambient environment.

100. A charge-flow transistor comprising: a semiconductor substrate; a source region; a drain regin; a gate insulator; a gapped gate electrode; and a thin-film sensor material disposed in the gap of said gapped gate electrode, said sensor material having electrical conductance that is sensitive to a property of the ambient environment within which the transistor is located and said sensor material having a surface conductance that differs substantially from the bulk conductance thereof, said thin-film sensor material being poly (imidazole) from 1,4-bis (phenylglyoxyloyl) benezene and ferrocene-1,1'-dicarboxaldehyde.

* * * * *